United States Patent [19]

Chick et al.

[11] 4,242,459
[45] Dec. 30, 1980

[54] CELL CULTURE DEVICE

[76] Inventors: William L. Chick, 32 Willow Rd., Wellesley, Mass. 02181; Pierre M. Galletti, 36 Taber Ave.; Peter D. Richardson, 60 Sargent Ave., both of Providence, R.I. 02906; Georg Panol, 165 Shenandoah Rd., Warwick, R.I. 02886

[21] Appl. No.: 957,303

[22] Filed: Nov. 2, 1978

[51] Int. Cl.³ .............................................. A01N 1/02
[52] U.S. Cl. ................................... 435/283; 435/284; 435/286; 210/321.2; 128/DIG. 3
[58] Field of Search ................. 195/127, 139, 1.7, 1.8; 128/DIG. 3; 210/321 B, 22; 422/44, 48; 435/284, 283, 286, 313, 818; 3/1

[56] References Cited

U.S. PATENT DOCUMENTS

| | | | |
|---|---|---|---|
| 3,131,143 | 4/1964 | Ferrari | 210/22 |
| 3,388,803 | 6/1968 | Scott | 210/321 |
| 3,734,851 | 5/1973 | Matsumura | 210/22 |
| 3,821,087 | 6/1974 | Knazek et al. | 195/127 |
| 3,827,565 | 8/1974 | Matsumura | 210/22 |
| 3,883,393 | 5/1975 | Knazek et al. | 195/1.8 |
| 4,144,136 | 3/1979 | Corbeil | 195/127 |

FOREIGN PATENT DOCUMENTS 1027304  3/1978  Canada.

OTHER PUBLICATIONS

Whittemore et al., "Effects of the Hybrid Artificial Pancreas in Diabetic Rats", vol. XXIII, Trans. Am. Soc. Artif. Intern. Organs, 1977, pp. 336-340.
Tanishita et al. "Tightly Wound Coils of Microporous Tubing", vol. XXI, Trans. Amer. Soc. Artif. Int. Organs, 1975, pp. 216-223.
Chick et al., "A Hybrid Artificial Pancreas", vol. XXI, Trans. Amer. Soc. Artif. Int. Organs, 1975, pp. 8-14.

*Primary Examiner*—R. B. Penland

[57] ABSTRACT

A cell culture device for use, e.g., as an artificial pancreas, featuring, in various aspects, a tightly wound spiral tube snugly fit in a cavity to form a cell culture compartment, the spiral being eccentrically offset in the cavity to reduce the volume of the compartment, a sloped passage in the body with an end of the tube extending through the passage to the innermost spiral without bending sharply, the ends of the spiral tube communicating with ports on the same side of the body, and a wall of the cavity facing the spiral and being spaced from the tube to form an end of the compartment to provide for simplified cell loading.

20 Claims, 4 Drawing Figures

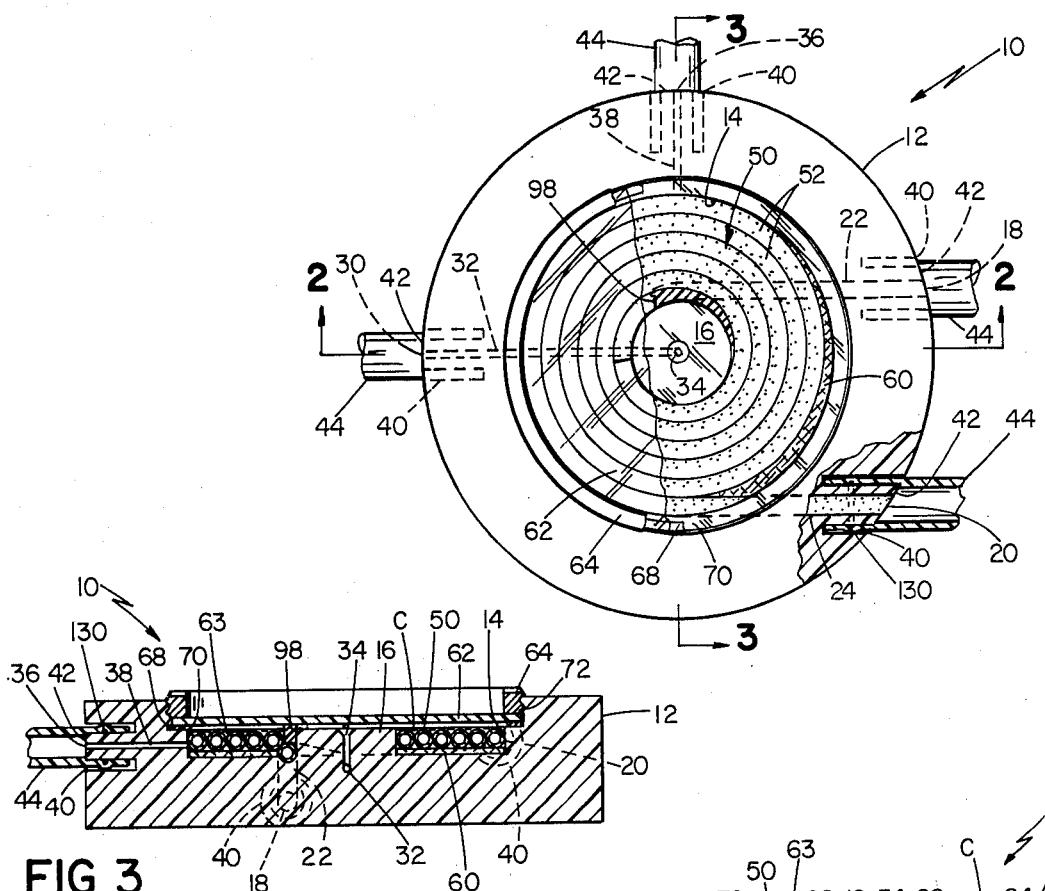

CELL CULTURE DEVICE

The invention described herein was made in the course of work under a grant or award from the Department of Health, Education, and Welfare.

FIELD OF THE INVENTION

This invention relates to cell culture devices for medical use, such as a prosthesis which can be substituted for the endocrine pancreas.

BACKGROUND OF THE INVENTION

Prior cell culture devices have used three dimensional polymeric matrices comprising bundles of parallel fibers potted together at each end to form artificial capillary beds. See, e.g., Knazek et al. U.S. Pat. No. 3,821,087. However, one problem with such devices is that when used with blood, clotting tends to occur at the ends of the fibers.

Spielberg Canadian Pat. No. 1,027,304 shows an artificial gland, in which a single blood flow path is defined by a semipermeable membrane coiled in helical form. Devices such as that disclosed in Spielberg have undesirably long response times when used, e.g., as an artificial pancreas, because of the great diffusion distances between the cell culture and the blood flow path.

Prior efforts of the present inventors on both parallel and coiled devices are described in Chick et al., A Hybrid Artificial Pancreas, Vol. XXI Trans.Amer.Soc.Artif.Int.Organs, 1975 and Whittemore et al., Effects of the Hybrid Artificial Pancreas in Diabetic Rats, Vol. XXIII Trans.Am.Soc.Artif.Intern.Organs, 1977.

SUMMARY OF THE INVENTION

The invention provides a cell culture device which avoids undesirable clotting and which has a short response time. The device is easy to charge with pancreatic cells for use as a reliably effective artificial pancreas.

In one aspect the invention features a body having a fluid tight cavity, and a semi-permeable tube wrapped about an axis to form coils in the cavity, the interior of the tube defining a fluid flow path for communicating with a fluid source, the walls of the cavity and the exterior of the tube defining a cell culture compartment, the tube being tightly wound such that adjacent coils touch each other, and the cavity being just wide enough and high enough to provide a snug fit for the tightly wound coils. In preferred embodiments the tube is wrapped to form a flat spiral; the cavity is circular in cross section, and the axis is eccentrically offset with respect to the cavity by one outside diameter of the tube to reduce the volume of the compartment; the tube is wrapped around an eccentrically offset circular cylindrical winding post; the post has a bore communicating with an exterior port for charging the compartment with cells; the body has a vent for applying a vacuum to the compartment to draw the cells in during charging; and an optically clear removable plate forms one wall of the cavity to enable the compartment and coils to be viewed, and to provide access to the cavity.

In another aspect the invention features a first port in an exterior side surface of the body, and a sloped passage in the body extending beneath the coils, between the cavity and the port, one end of the tube extending from the innermost coil, through the passage, to the port, without bending sharply. In preferred embodiments there is a second port in the same side surface of the body adjacent the first port, and a second passage in the body extending between the second port and the cavity, the other end of the tube extending from the outermost coil of the tube, through the second passage, to the second port, to provide for simple attachment of the ends of the coil to the user from the same side of the body of the device.

In yet another aspect the invention features a wall of the cavity facing the spiral and being spaced along the axis away from the coils to form an end portion of the compartment, the body having a port in its exterior surface and a passage communicating between the port and the end portion, thereby enabling the compartment to be charged with cells through the port, the cells distributing through the compartment from the end portion. In preferred embodiments the passage communicates with the compartment through a bore in a winding post.

PREFERRED EMBODIMENT

We turn now to the structure and operation of a preferred embodiment, first briefly describing the drawings thereof.

DRAWINGS

FIG. 1 is a plan view, partially in section and broken away, of an artificial pancreas embodying the invention.

FIG. 2 is a view taken along 2—2 of FIG. 1.

FIG. 3 is a view taken along 3—3 of FIG. 1.

FIG. 4 is a perspective view, somewhat schematic, showing an apparatus for assembling the pancreas of FIG. 1, with the pancreas being shown in an intermediate stage of construction.

STRUCTURE AND METHOD OF CONSTRUCTION

There is shown in FIG. 1 an artificial pancreas 10 having a disc-shaped body 12 with an annular cavity 14 surrounding a circular, eccentrically positioned winding post 16. Blood inlet port 18 and outlet port 20 communicate with cavity 14 through passages 22 and 24. Cell charging port 30 communicates with cavity 14 through passage 32 and bore 34 in post 16. Vent 36 communicates with cavity 14 through passage 38. Annular slots 40 cut in body 12 surround ports 18, 20, 30 and vent 36, forming integral connectors 42 for nipples 44.

A perfusion tube 50 is wrapped around post 16 forming spiral coils 52 in cavity 14. One end of tube 50 extends through sloped passage 22 to inlet port 18, and the other end through passage 24 to outlet port 20.

Turning now to FIGS. 2 and 3, tube 50 is positioned in cavity 14 between annular mesh 60 surrounding post 16 and circular cover plate 62 to form cell culture compartment 63. A threaded stainless steel ring 64 seals cover plate 62 against a flat gasket 68 on circumferential shoulder 70.

To prepare body 12, a 50 mm diameter circular disc is cut from ⅜ inch thick optically clear Plexiglas and milled to form cavity 14 and post 16. Post 16 is eccentrically offset by one outside diameter of tube 50, and the cavity is just wide enough to provide a snug fit for coils 52. Slots 40 are cut into body 12. Ports 18, 20, 30, vent 36, passages 22, 24, 32, 38, and bore 34 are drilled in body 12. Shoulder 70 is milled and threads 72 are cut above the shoulder. The shoulder is cut to provide a cavity 14 just high enough to accommodate mesh 60 and coils 52 with approximately 0.5 mm clearance.

Turning now to FIG. 4, to form coils 52, body 12 is fixed on a rotating horizontal platform 80, which is axially mounted on a slow-turning servo-controlled motor 82. Tube 50 (XM-50, high flux 50,000 molecular weight cut-off material, 1.10 mm I.D., 1.46 mm O.D., stabilized by immersion in a 20% glycerin solution, manufactured by Amicon Corporation, Lexington, Mass.) is placed in a trough 84, which is positioned at a slight vertical angle to platform 80. The lead end of tube 50 is first threaded through the center of mesh 60 (Nitex, 5μ mesh), and is then advanced from cavity 14 through passage 22, until it extends about 3 cm outwardly from port 18. A Teflon plug 86 is inserted into the lead end of tube 50 and attached to an arm 88 extending from platform 80, thereby fixing that end of the tube to the platform. Mesh 60 is slipped along tube 50 and positioned at the bottom of cavity 14. The other end of tube 50 is cemented with cyanacrylic glue to one end of an 8 foot polyethylene tube 90, which is vertically suspended by a spring 92. The other end of tube 90 is connected to a source 94 of pressurized $CO_2$, and tube 50 is pressurized at 10 psig.

Motor 82 is activated to rotate platform 80 (at one rpm) until a half coil of tube 50 is wound around post 16. (The pressurized $CO_2$ gas prevents the thin-walled tube 50 from kinking and continually seeps through the pores of the tube to act as a lubricant to minimize friction between the tube and trough 84.) A falciform Plexiglas element 98 is positioned over the first half coil and glued to post 16. Winding then continues until the first coil 52 is completely wound, the tube abutting against the falciform element to prevent the next coil from crossing over the innermost coil and crushing it.

A temporary cover plate 110 is placed over cavity 14 on top of post 16, tube 50 passing through a bevelled opening 112 in the plate. Plate 110 is held stationary with respect to rotating platform 80 by vertical support 116. Further coil winding now proceeds at the same low speed until six coils are wound (corresponding to approximately 55 cm of tubing 50). The cover plate 110 prevents coils 52 from popping upwardly during winding.

Just before the last coil is completely wound, one end of a thin PVC tube 118 is threaded through outlet port 20 and passage 24 into cavity 14. Tube 50 is cut from tube 90 and glued to the end of tube 118. Tube 118 is then pulled back out through body 12, carrying the end of tube 50 out through port 20.

The tube 50 is cut flush at both ends with connectors 42. A wire 130 is wrapped around the end of each connector 42, and a nipple 44 is glued to each connector with Amicon 674 epoxy.

Temporary plate 110 is removed. Gasket 68 (medical grade silicon rubber, 0.3 mm thick) is positioned on shoulder 70. Cover 62 (optically clear Plexiglas) is placed over the gasket, and ring 64 is screwed into place to seal the cover against the gasket.

OPERATION

In use, pancreas unit 10 is sterilized with ethylene oxide and then degassed in a vacuum. A sterile culture medium is flushed through the unit for several days to remove any remaining debris. Cavity 14 is then loaded with a suspension C of pancreatic cells and culture medium. (This loading is best accomplished by drawing the material into the cavity, from a syringe inserted in charging port 30, with a suction produced by a syringe inserted in vent 36.) Port 30 and vent 36 are now sealed, and the loaded unit is incubated for one week in air with 5% $CO_2$ at 37° C.

The unit is now ready to be mounted by connecting an artery of the user to inlet 18 and a vein to outlet 20 by an externalized shunt. The inlet and outlet ports are adjacent one another and enter and leave body 12 from the same direction to allow for easy connection to the user. The user's blood circulates through semipermeable perfusion tube 50. A rise in the blood glucose level is sensed by the pancreatic cells, causing them to produce insulin, which enters the user's bloodstream through the wall of the semipermeable tube.

In addition to allowing insulin and waste products from the cells to enter the bloodstream, the wall of the semipermeable tube also permits the transport of oxygen and essential nutrients from the blood to sustain the cells, and prevents direct contact between cultured cells, leucocytes, and antibodies to provide immunological separation of the cavity and the coils.

The tightly enclosed cell culture compartment, with a minimum of "dead space", provides short diffusion distances between the cells and the bloodstream, enabling the device to respond quickly to blood glucose changes.

OTHER EMBODIMENTS

Other embodiments are within the following claims. For example, while the unit has been described for use as an externalized shunt, it could also be adapted to be implanted.

The ends of perfusion tube 50 could be extended outside body 12 and adapted for use as cannulae for direct insertion into the blood vessels. (Each extended end of tube 50 would then be cut at an angle and coated with epoxy to provide a sharp, rigid tip, and the portion of the tube external to body 12 coated with polyurethane or silicone elastomer to render it flexible and impermeable to water.) Advantageously, blood flowing through the unit would then only contact a single material.

Of course, different perfusion tubing 50 (e.g., larger diameter, thinner wall, different exclusion point) could be used depending on the specific application of each device. For example, larger diameter tubing (e.g., XM-50, 2.40 mm I.D., 2.70 mm O.D., high flux molecular weight cut-off material, manufactured by Amicon) could be used for those applications where clotting is particularly troublesome, or a thinner wall could be used when response time is critical.

The unit has other important applications as well. It could be adapted for use as an artificial liver by loading it with a liver cell suspension. Also, the unit could be used to obtain large quantities of heretofore difficult-to-collect material produced by living cells. For example, it is known that cancer cells produce certain proteins which, until now, have only been obtainable in trace quantities. Large amounts of these proteins could be obtained by loading cavity 14 with cancer cells, applying a source of pressurized water and nutrient solution to the inside of perfusion tube 50, and opening vent 36 through a mesh screen; the water would continually wash through the cavity to flush the protein out the screened vent to a collector.

What is claimed is:

1. A cell culture device comprising, a body having a generally circular fluid tight cavity therein, said body having an inlet and an outlet and a semi-permeable tube wrapped about itself to form coils in said cavity, said coils forming a flat spiral about a central axis, the interior of said tube providing a fluid flow path for communicating with a biological fluid source, said flat spiral coils positioned in said cavity between a bottom wall and a cover plate to form a cell culture compartment therebetween, said tube being tightly wound in said flat spiral such that adjacent coils thereof touch each other to substantially eliminate dead space between said coils, the ends of said tube extending through said inlet and said outlet, and said cavity being shaped to entirely surround said coils and being just wide enough and high enough to accommodate said tightly wound coils, to further reduce dead space.

2. The cell culture device of claim 1 wherein,
said cavity is circular in cross section, and
said axis is eccentrically offset with respect to said cavity to reduce the volume of said compartment.

3. The cell culture device of claim 2 wherein,
said axis is eccentrically offset by one outside diameter of said tube.

4. The cell culture device of claim 1 further comprising,
a winding post positioned within said cavity,
said tube being wrapped around said post to form said coils.

5. The cell culture device of claim 4 wherein,
said cavity is circular, and
said winding post is a circular cylinder eccentrically offset with respect to said cavity by one outside diameter of said tube.

6. The cell culture device of claim 4 wherein,
said body has a port in the exterior surface thereof,
said post has a bore therein communicating with said compartment, and
said body has a passage therein communicating between said port and said bore,
whereby said compartment may be charged with cells through said port.

7. The cell culture device of claim 6 wherein,
said body has a vent communicating with said compartment,
whereby cells may be drawn into said compartment through said port by a vacuum applied to said compartment through said vent.

8. The cell culture device of claim 1 wherein,
a side of said body forming a wall of said cavity is optically clear,
whereby said compartment and said coils are viewable therethrough.

9. The cell culture device of claim 1 wherein,
said cover plate is removable to provide access to said cavity.

10. The cell culture device of claim 9 wherein,
said plate is optically clear,
whereby said compartment and said coils are viewable therethrough.

11. The cell culture device of claim 1 wherein
said inlet comprising a first port in an exterior side wall of said body,
a sloped first passage in said body extending beneath said coils, between said cavity and said port,
one end of said tube extending from the coil of said spiral closest to said axis, through said passage, to said first port,
said outlet comprising a second port in an exterior side wall of said body adjacent to said first port, and
a second passage in said body extending between said second port and said cavity,
the other end of said tube extending from the outermost coil of said tube, through said second passage, to said second port.

12. The cell culture device of claim 11 wherein,
said first and second passages lie in parallel planes.

13. The cell culture device of claim 11 wherein,
said first and second ports are on the same side of said body.

14. The cell culture device of claim 11 further comprising,
a winding post positioned within said cavity,
said tube being wrapped around said post to form said coils.

15. The cell culture device of claim 14 wherein, said post is circular in cross section, and further comprising,
a falciform element positioned between said post and the innermost coil of said tube to prevent the next adjacent coil of said tube from crossing over the innermost coil.

16. The cell culture device of claim 1 wherein said bottom wall of said flat spiral coils being spaced away from the coils to form a chamber in said compartment between said wall and said coils,
said body having an exterior surface and cell-charging port through said exterior surface and a passage communicating between said port and said chamber,
whereby said compartment may be charged with cells through said port, the cells distributing through said compartment from said chamber.

17. The cell culture device of claim 16 wherein said passage communicates with said chamber at the axis of said flat spiral coils,
whereby said cells distribute substantially radially.

18. The cell culture compartment of claim 16 further comprising,
a winding post positioned within said cavity,
said tube being wrapped around said post to form said coils,
said post having a bore therein, and
said passage communicating with said chamber through said bore.

19. The cell culture device of claim 16 wherein,
said bottom wall is spaced no more than 0.5 mm from said coils.

20. The cell culture device of claims 1 or 9 further comprising,
a mesh element positioned between said coils and said bottom wall of said cavity perpendicular to said central axis.

* * * * *